(12) United States Patent
Dimas

(10) Patent No.: US 9,387,333 B2
(45) Date of Patent: Jul. 12, 2016

(54) IDENTIFIER DEVICE FOR IMPLANTABLE DEFIBRILLATORS AND PACEMAKERS

(71) Applicant: Vassilis Dimas, Dallas, TX (US)

(72) Inventor: Vassilis Dimas, Dallas, TX (US)

(*) Notice: Subject to any disclaimer, the term of this patent is extended or adjusted under 35 U.S.C. 154(b) by 62 days.

(21) Appl. No.: 14/488,538

(22) Filed: Sep. 17, 2014

(65) Prior Publication Data

US 2016/0074665 A1 Mar. 17, 2016

Related U.S. Application Data

(60) Provisional application No. 61/878,807, filed on Sep. 17, 2013.

(51) Int. Cl.
| G08B 21/00 | (2006.01) |
| A61N 1/372 | (2006.01) |
| H04Q 9/00  | (2006.01) |

(52) U.S. Cl.
CPC ........ *A61N 1/37229* (2013.01); *A61N 1/37252* (2013.01); *H04Q 9/00* (2013.01)

(58) Field of Classification Search
CPC .. A61N 1/37229; A61N 1/37252; H04Q 9/00
USPC .................................................. 340/870.07
See application file for complete search history.

(56) References Cited

U.S. PATENT DOCUMENTS

| 2003/0018369 | A1* | 1/2003 | Thompson | A61N 1/37252 607/60 |
| 2003/0114897 | A1* | 6/2003 | Von Arx | A61N 1/37223 607/60 |
| 2007/0260293 | A1* | 11/2007 | Carpenter | A61N 1/3727 607/60 |
| 2010/0114242 | A1* | 5/2010 | Doerr | A61N 1/37235 607/59 |
| 2013/0245720 | A1* | 9/2013 | Rahman | A61N 1/37229 607/60 |
| 2013/0268029 | A1* | 10/2013 | Cauller | A61B 5/6849 607/61 |
| 2014/0019076 | A1* | 1/2014 | Horton | A61N 1/3718 702/73 |
| 2015/0073500 | A1* | 3/2015 | Kothandaraman | A61N 1/37252 607/59 |

\* cited by examiner

*Primary Examiner* — Mark Rushing

(57) ABSTRACT

An identifier apparatus 10 for acquiring a signature signal frequency 12 from an implantable medical device 11 that is internally implanted in a patient. The apparatus 10 identifies the type of implantable medical device 11 and the device manufacturer by the unique signature signal frequency 12 of the manufacturer and device. The apparatus 10 aids healthcare providers with quick and exact knowledge of a patients implanted device.

4 Claims, 4 Drawing Sheets

IDENTIFIER DEVICE FOR IMPLANTABLE DEFIBRILLATORS AND PACEMAKERS

CROSS-REFERENCE TO RELATED APPLICATIONS

This application claims the benefit of provisional patent application, application Ser. No. 61/878,804, filed Sep. 17, 2013 by the present inventor Vassilis Dimas.

FIELD OF THE INVENTION

The present invention relates to a hand-held scanner to identify specific frequencies of radio waves emitted by devices surgically implanted in a body of a person, and match that emitted frequency to an associated manufacturer of the implanted device.

BACKGROUND OF THE INVENTION

The miracles of modern medicine continue to amaze. Cardiac implantable electrical devices (CIED's), which include implantable pacemakers, defibrillators, and implantable loop recorders, have been around for decades, and utilize the latest in electronics and computer technology. Such technology allows for small size, precise operation, increasingly improving battery longevity, recording of diagnostic data, and tailoring of operating parameters to individual patient needs. The end result is that millions of patients in the US, and abroad, benefit from CIED's with hundreds of thousands of new patients receiving implants every year. This results in an unusual challenge to healthcare providers who are caring for patients with CIED's. Healthcare providers commonly require accessing of CIED diagnostic data and performed using RF telemetry enabled programmers supplied by the various manufacturers of the CIED's, which are not compatible with other manufactures CIED's. This has created an interesting dynamic within the healthcare world where trained programmer operators (often manufacturer representatives) are frequently called into clinical settings to use their programmer to interact with a patient's CIED and then provide valuable device information to the overseeing healthcare provider. This reliance on trained programmer operators occurs in virtually every clinical setting imaginable including physician offices, hospital settings, long-term care facilities, nursing homes, outpatient surgery centers, and emergency rooms. Typically, these trained programmer operators are not on site in these settings, so quick identification of a patient's CIED manufacturer is a necessary first step to facilitate notification of the appropriate programmer operator in a timely fashion. Despite significant advances in device related technology, methods for CIED manufacturer identification remain antiquated and have not kept pace with our evolving healthcare system that relies on efficiency to reduce cost and improve patient outcomes. Current methods for CIED manufacturer identification include identification cards carried by the patient, directly calling all CIED manufacturers and having them look up the patient in their databases, or chest x-ray. Identification cards are often lost by the patients or left in a wallet or purse that is not with the patient in the clinical setting. Frequently, the provider must make a guess regarding the CIED manufacturer during a patient visit, but this method may require a phone call to as many as all CIED manufacturers prior to appropriate identification of the correct manufacturer. This is a time consuming process that can utilize anywhere from fifteen to forty-five minutes (15-45 mins.) of a healthcare provider's time. A chest x-ray is not only a source of unnecessary radiation exposure as well as cost, but it also is not a definitive method for manufacturer identification. In the end, current methods for CIED manufacturer identification result in poor utilization of healthcare resources, decreased efficiency, and healthcare dollars unnecessarily wasted on what could be a relatively simple task. Accordingly, there exists a need for a means by which CIED's can be quickly, easily, and reliably identified in order to avoid these problems. The development of the present invention fulfills this need.

DRAWINGS FIGURES

The advantages and features of the present invention will become better understood with reference to the following more detailed description and claims taken in conjunction with the accompanying drawings, in which like elements are identified with like symbols, and in which:

FIG. 1 is a perspective view of a scanner 20 and charging station 30 to identify implantable medical devices 11, according to a preferred embodiment of the present invention.

DRAWINGS Reference Numerals

| | |
|---|---|
| 10 apparatus | 110 second antenna |
| 11 implantable medical device | 120 switching assembly |
| 12 signature frequency | 130 rechargeable battery |
| 20 scanner | 140 first set of electrical leads |
| 30 charging station | 150 second set of electrical leads |
| 40 central processor | 160 trays |
| 50 interface | 170 base |
| 60 display screen | 180 charging port |
| 70 handle | 190 electrical power cord |
| 80 wand | 200 powers converted |
| 90 first antenna | 210 transformers |
| 100 electrical circuitry | 220 wirelesses MODEM |

DESCRIPTION OF THE INVENTION

The best mode for carrying out the invention is presented in terms of its preferred embodiment, herein depicted within FIGS. 1 through 4. However, the invention is not limited to the described embodiment, and a person skilled in the art will appreciate that many other embodiments of the invention are possible without deviating from the basic concept of the invention and that any such work around will also fall under the scope of this invention. It is envisioned that other styles and configurations of the present invention can be easily incorporated into the teachings of the present invention, and only one particular configuration shall be shown and described for purposes of clarity and disclosure and not by way of limitation of scope. The terms "a" and "an" herein do not denote a limitation of quantity, but rather denote the presence of at least one of the referenced items.

DETAILED DESCRIPTION FIGURES

Figure 1:
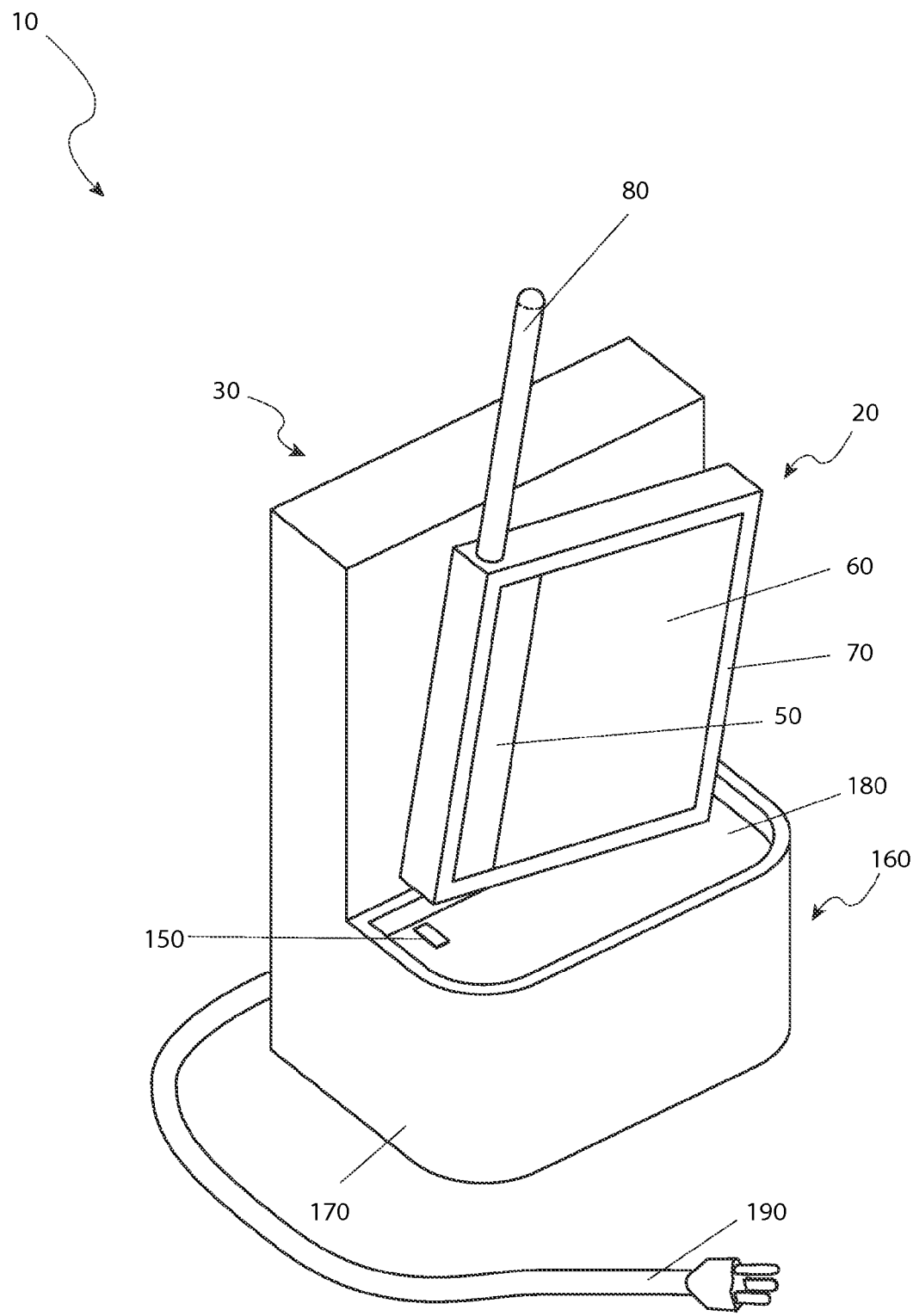
Figure 2:
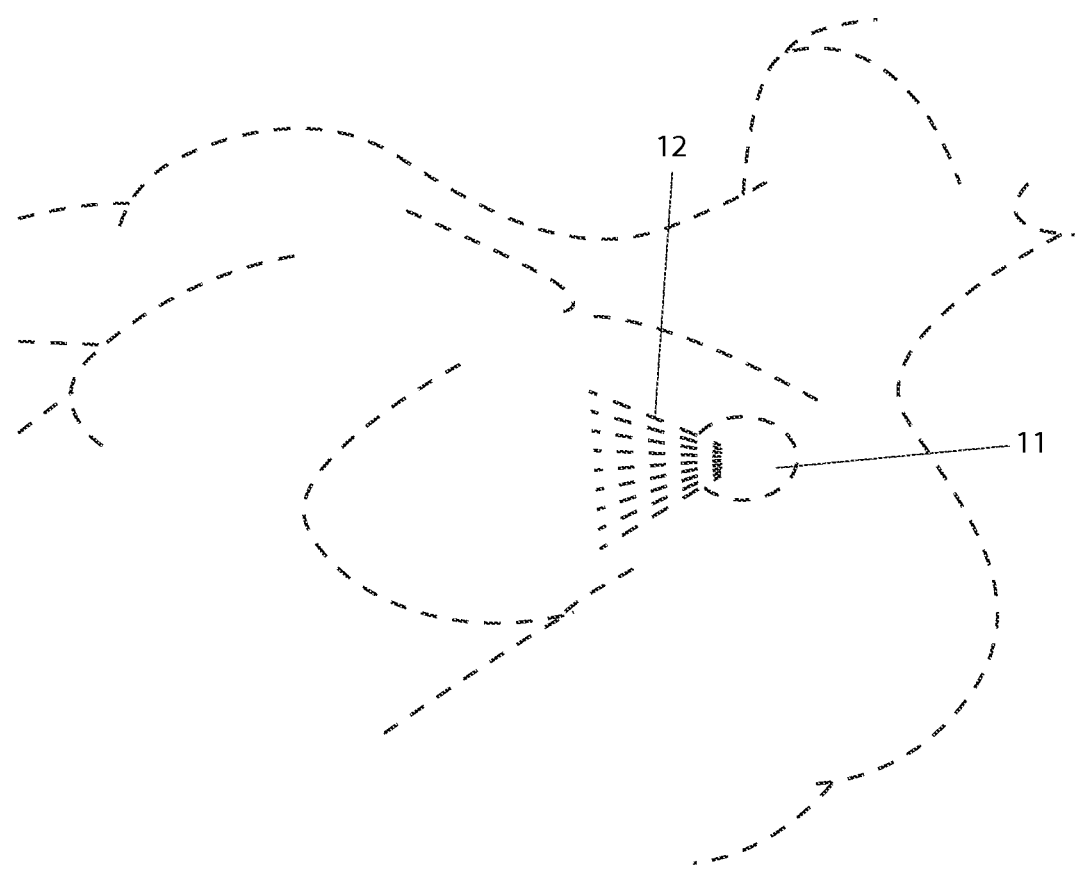
FIG. 2 is an environmental view of an implantable medical device 11 emitting a signature frequency 12, according to a preferred embodiment of the present invention.
Figure 3:
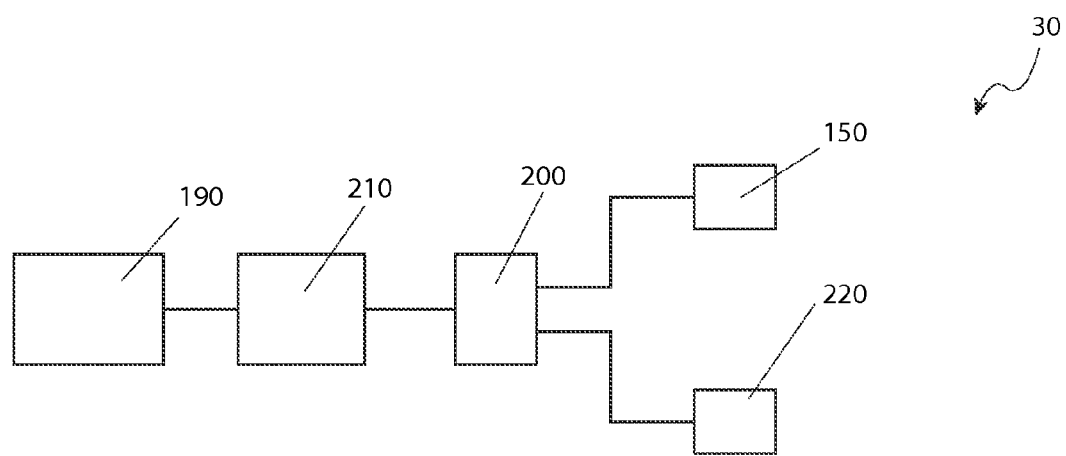
FIG. 3 is an electrical schematic of the charging station 30, according to a preferred embodiment of the present invention.
Figure 4:
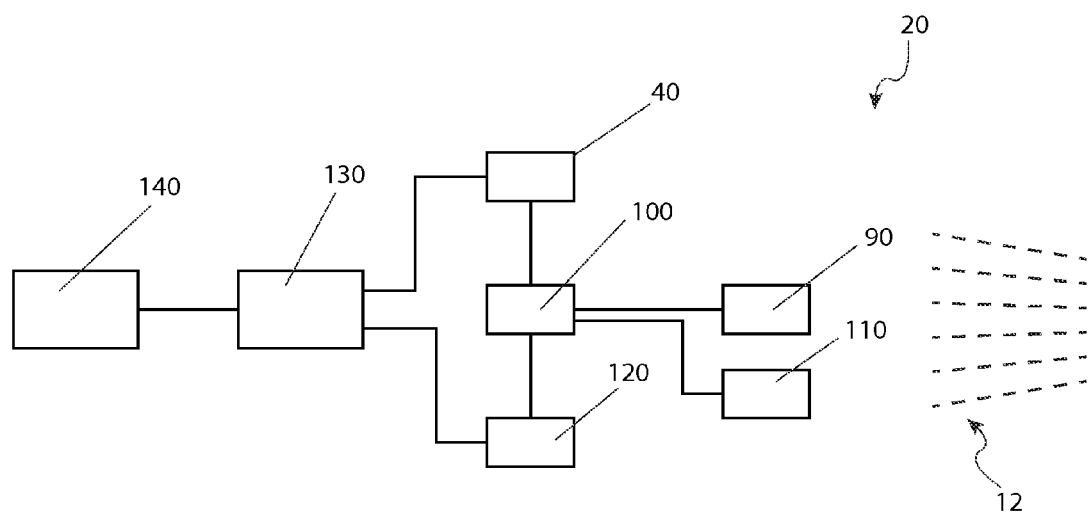
FIG. 4 is an electrical schematic of the scanner 20, according to a preferred embodiment of the present invention.

The present invention describes a hand-held apparatus (herein referred to as the "apparatus") particularly suited to record frequencies of radio waves emitted by devices 11 surgically implanted in a body of a person, identify specific signature frequencies 12, and match those frequencies 12 to an associated manufacturer of the implanted device 11. Referring now to FIGS. 1 and 2, perspective view of a scanner 20 and charging station 30 to identify implantable medical devices 11 and an environmental view of an implantable medical device 11 emitting a signature frequency 12, according to a preferred embodiment of the present invention, are disclosed. The apparatus 10 comprises a scanner 20 and a charging station 30. The scanner 20 is used to detect and identify certain frequencies of radio waves emitted from medical devices 11 that are surgically implanted into a person. Implantable medical devices 11, such as defibrillators and pacemakers, are "interrogatable". Interrogation comprises collecting status and performance data that have been encoded into carrier electromagnetic waves emitted by the device 11, analyzing the data, and converting the date into an assessment of the patient who has the device 11 implanted in their being. These medical devices 11 typically emit electromagnetic waves, in the radio wave spectrum, encoded with the data that are acquisitioned and processed to provide the assessment of the patient. The radio wave spectrum is a band of electromagnetic waves exhibiting a frequency within the range of three hundred gigahertz to three kilohertz (300 GHz to 3 kHz) (herein referred to as "RF"). In addition to the status and performance data, each device 11 emits a signature electromagnetic wave, exhibiting a specific frequency, (herein referred to as "signature frequency") 12. This signature frequency 12 is unique to the manufacturer of the device 11; therefore, it can be used to identify the manufacturer of the device 11. It is this signature frequency 12 that the scanner 20 detects and associates with a particular manufacture. There are multiple manufacturers of such devices 11, but each device 11 manufactured from a particular manufacturer emits a signature frequency 12 that is unique to that manufacture. Each signature frequency 12, along with its associated manufacturer, is assigned a proxy value, which is stored in a database of a central processor 40 (see FIG. 4) housed within the scanner 20. The scanner 20, through a Fourier Transform signal processing scheme, identifies frequencies of RF waves emitted from the devices 11, converts them to binary information, and processed the binary information through an algorithm of the central processor 40 (see FIG. 4) to match the bit sequence of the binary information to one (1) of the stored proxy values of the database. Once a match has been made, the central processor 40 (see FIG. 4) communicates a signal to a display screen 60 of the scanner 20 to present a digital readout that indicates the manufacturer associated with the signature frequency 12. The scanner 20 comprises a handle 70 and a wand 80, and is preferably fabricated from a rigid plastic material. The handle 70 has a hollow construction that houses the central processor and the necessary electrical circuitry 100 (see FIG. 4) for the scanner 20. The wand 80 extends from a top portion of the handle 70, and is an elongated member that houses a first antenna 90 (see FIG. 4). It is understood that other configurations and ornamental designs of the scanner 20 may be utilized without deviating from the teaching of the apparatus 10. The first antenna 90 (see FIG. 4) is an induction style antenna and preferably comprises electrically conductive elements configured to form an induction coil. The length and configuration of the first antenna 90 is such that it generates alternating current when placed in a RF wave field. The electrical circuitry 100 (see FIG. 4) is placed into electrical communication with the first antenna 90 (see FIG. 4) so that electrical current generated by the first antenna 90 (see FIG. 4) is transmitted to the electrical circuitry 100 (see FIG. 4). When the first antenna 90 is within a RF wave field, induction generates an alternating electrical current exhibiting a frequency mirroring the frequency of the RF waves being imparted upon the first antenna 90 (5 see FIG. 4), which is then transmitted to the electrical circuitry 100 (see FIG. 4). Referring now to FIG. 4, an electrical schematic of the scanner 20, according to a preferred embodiment of the present invention, is disclosed. The electrical circuitry 100 preferably comprises a plurality of resonant circuits, response circuits, excitation circuits, and feedback circuits so as to enable the scanner 20 (see FIG. 1) to serve as a transmitter, a receiver, and an analog frequency detector. The electrical circuitry 100 is further configured to create a plurality of circuit arrays, arranged in parallel, where each array operates at a resonant frequency. The resonant frequency is a frequency of alternating current passing through the array at which resonance will occur. The circuitry is configured such that resonance is a condition precedent for the circuit to operate. Configuration of the feedback and response circuits further enables a user to tune each resonant circuit to operate at a desired resonant frequency, thereby setting a resonant frequency for each array at the discretion of the user. To make the electrical circuitry 100 act as an identifier of signature frequencies 12 (see FIG. 2), each resonant frequency set for each array will be the signature frequency 12 (see FIG. 2) associated with the various implantable medical devices 11 (see FIG. 2) that a user desires to identify. Therefore, each array is tuned to resonate at a frequency associated with the signature frequency 12 (see FIG. 2) of an implantable medical device 11 (see FIG. 2) made by a particular manufacturer. The alternating electrical current transmitted from the first antenna 90, if it matches that of one (1) of the resonant frequencies of an array, will cause that array to operate. Once in operation, an excitation circuit of the activated array emits a communication signal that is transferred to the central processor 40. This communication signal is concurrently emitted from the scanner 20 (see FIG. 1) by a second antenna 110. The second antenna 110 has a similar construction and configuration as that of the first antenna 100, and is placed into electrical connection with each excitation circuit. The excitation circuit sends alternating current to the second antenna 110, which radiates RF waves exhibiting a frequency mirroring the frequency of the alternating current of the excitation circuit. Again, configuration of the feedback and response circuits further enables a user to adjust the frequency of the alternating current being transmitted by each excitation circuit. This affords a user the ability to set a frequency for each communication signal from each excitation circuit so that a particular communication signal is characteristic of the wireless signal necessary to establish communication with the implantable medical device 11 (see FIG. 2). It is understood that amplifier, attenuation, and filter circuitry necessary to facilitate adequate signal telemetry between the scanner 20 (see FIG. 1) and any implantable medical device 11 (see FIG. 2) within operational range of each other are incorporated into the electrical circuitry 100. It is envisioned for the operational range to be between three inches (3 in.) and 24 inches (24 in.). The central processor 40 is in electrical communication with the electrical circuitry 100. The central processor 40 creates binary outputs by performing algorithmic functions of a computer program based upon conditional binary inputs. A signal analysis algorithmic function of the central processor 40 preferably exploits a Fourier Transform function to enable signal processing of the analog radio wave signal transmitted from the first antenna 90. The Fourier Transform function samples the signal and provides a binary output representative of the signal. This binary output is encoded and then iterated through another algorithm of the central processor 40 to determine a match within the proxy value database of the central processor 40. The central processor 40 is further provided with algorithmic functions to manipulate the feedback and response circuits in order to set resonant frequencies and communication signal frequencies of circuit arrays based upon manual inputs through an interface 50 (see FIG. 1) of the scanner 20 (see FIG. 1), or through wireless download inputs when the scanner 20 (see FIG. 1) is connected to the charging station 30 (see FIG. 1). A front surface of the handle 70 (see FIG. 1) of the scanner 20 (see FIG. 1) is provided an interface 50 (see FIG. 1) and display screen 60 (see FIG. 1). The interface 50 (see FIG. 1) enables a user to command the apparatus by manual inputs. The interface 50 (see FIG. 1) preferably is a touch-screen, having depression plates and pressure sensors in electrical connections with a switching assembly 120. When depressed, an electrical contact is made between a depression plate and pressure sensor to send an electrical signal to the central processor 40 to carry out a command. The display screen 60 (see FIG. 1) is a digital display, and preferably comprises an array of liquid crystals. When prompted by an algorithmic function, due to a conditional input, the central processor 40 sends an electrical signal to the display screen 60 (see FIG. 1) to excite a an array, or multiple arrays, of liquid crystals to generate a pixel image on the display screen 60 (see FIG. 1). A rechargeable battery 130 is located with the handle 70 (see FIG. 1). The battery 130 preferably comprises an electrochemical cell having an anode and cathode to convert and store electrical energy; however, it is understood that other battery 130 styles and types may be utilized without deviating from the teachings of the apparatus 10, and as such should not be interpreted as a limiting factor of the apparatus 10. Extending from the battery 130 is a first set of electrical leads 140 that terminate at a bottom surface of the handle 70 (see FIG. 1). The first set of electrical leads 140 are also placed into electrical communication with the electrical circuitry 100. The first set of electrical leads 140 terminates at a surface of the handle 70 (see FIG. 1) such as to be exposed, thus facilitating electrical contact with a second set of electrical leads 150 (see FIG. 1) of the charging station 30 (see FIG. 1) when the scanner 20 (see FIG. 1) and placed into 20 the charging port 180 (see FIG. 1). Referring now to FIG. 3, an electrical schematic of the charging station 30, according to a preferred embodiment of the present invention, is disclosed. The charging station 30 (see FIG. 1) comprises a casing, having a tray 160 (see FIG. 1) positioned on top of a base 170 (see FIG. 1). The casing preferably comprises a rigid polymer material. A charging port 180 (see FIG. 1) is disposed on a surface of the tray 160 (see FIG. 1), where a surface of the charging port 180 is provided with the second set of electrical leads 150. It is understood that other configurations and ornamental designs of the charging station 30 may be utilized without deviating from the teaching of the apparatus 10. The second set of electrical leads 150 are configured to match a profile of the first set of electrical leads 140 (see FIG. 3) of the scanner 20 (see FIG. 1) so as to facilitate a physical contact between the two sets of leads 140, 150 when the handle 70 (see FIG. 1) of the scanner 20 (see FIG. 1) is inserted into the charging port 180 (see FIG. 1). The construction of the charging port 180 (see FIG. 1) and tray 160 (see FIG. 1) is such as to allow the scanner 20 (see FIG. 1) to rest in an up-right position on the tray 160 (see FIG. 1) while being docked in the charging port 180 (see FIG. 1). The charging port 180 (see FIG. 1) is further provided with a an electrical power cord 190, having a standard prong set to plug into a standard 120V wall outlet and draw electrical power from the outlet. The electrical power drawn from the wall outlet supplies the necessary electrical power to the charging station 30 (see FIG. 1) to recharge the battery 130 (see FIG. 4) of the scanner 20 (see FIG. 1) and operate the electrical components of the charging station 30 (see FIG. 1). A power converter 200 and transformer 210 are placed into electrical connection with the electrical power cord 190 where the electrical power cord 190 connects with the charging station 30 (see FIG. 1). The power converter 200 and transformer 210 configure the electrical power from the 120V power source to facilitate proper electrical power transfer to the battery 130 (see FIG. 4) of the scanner 20 (see FIG. 1) and electrical components of the charging station 30 (see FIG. 1). Electrical connections are made with the power converter 200 and transformer 210, which transfer the configured electrical power to the various electrical components of the charging station 30 (see FIG. 1) and to the second set of electrical leads 150 of the charging port 180 (see FIG. 1). The charging station 30 (see FIG. 1) is further equipped with a wireless MODEM 220 to facilitate modulation and demodulation of wireless communications, and the reception of wireless telemetric information from service providers. The MODEM 220 is placed into electrical connection with the second set of electrical leads 150 so that when the scanner 20 (see FIG. 1) is docked at the charging port 180 (see FIG. 1), the wireless telemetric information from service providers will automatically adjust algorithms of the central processor 40 (see FIG. 4), modify or add resonant frequencies, and modify or add communication signals. It is envisioned that other styles and configurations of the present invention can be easily incorporated into the teachings of the present invention, and only one particular configuration shall be shown and described for purposes of clarity and disclosure and not by way of limitation of scope.

Operation of the Preferred Embodiment

The preferred embodiment of the present invention can be utilized by the enabled user in a simple and straightforward manner with little or no training. The apparatus 10 would be configured as indicated in FIG. 1 upon the initial purchase or acquisition.

The method of utilizing the apparatus 10 may be achieved by performing the following steps: acquiring the apparatus 10; plugging the electrical power cord 190 in a wall outlet; docking the scanner 20 into the charging port 180 of the charging station 30; allowing the battery 130 to store electrical power; allowing the MODEM 220 to facilitate the transfer of updated information to modify computer algorithms of the central processor 40; removing the scanner 20 from the charging port 180; inputting commands manually through the interface 50 if necessary; grasping the handle 70 and placing the wand 80 within operational range of an implantable medical device 11 so that the first antenna 90 is within a RF wave field emitted by an implantable medical device 11; allowing the electrical circuitry 100, the central processor 40, and second antenna 110 communicate with the implantable medical device 11, identify a signature frequency 12, and display the associated manufacturer of the implantable medical device 11 on the display screen 60; and, employ the apparatus 10 to assist with the quick and accurate identification of a manufacturer of a surgically implanted medical device 11.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

I claim:
1. A telemetric device comprising:
a handle, having a hollow structure; an electrical circuit located within said handle; wherein said electrical circuit has at least one resonant circuit, at least one response circuit, at least one excitation circuit, and at least one feedback circuit; wherein said electrical circuit is configured to only operate when an alternating current of a particular frequency is received as an input; and, wherein said electrical circuit emits an alternating current circuit-signal of a certain frequency when in operation; a wand extending from a surface of said handle, having an elongated hollow structure; a first antenna located within said wand and placed into electrical communication with said electrical circuit, wherein said first antenna is configured to function as an inductive current coil when placed in a radio wave field; a second antenna located within said wand and placed into electrical communication with said electrical circuit, therein said second antenna is configured to radiate radio waves when alternating electrical current is passed through said second antenna; a central processor located within said handle and placed into electrical communication with said electrical circuit to create binary outputs by performing algorithmic functions of a computer program based upon binary inputs; and, wherein said central processor receives said circuit-signal from said electrical circuit, converts said circuit-signal to binary information, assigns a proxy value to said circuit signal, and acquisitions a matching value from a database; wherein said central processor sends a command-signal based upon a match between said proxy value and said database value from said database; and, a display screen located on a surface of said handle and placed into electrical communication with said central processor to display information regarding said matching value based upon said command-signal as said input.

2. The telemetric device recited in claim 1, further comprising:
a rechargeable electric battery located within said handle and placed into electrical connection with said electrical circuitry and said central processor; a first set of electrical leads extending from said battery and terminating at an outer surface of said handle; and, a charging station; wherein said charging station is provided with a base; wherein said base is provided with a tray; wherein said tray is provided with a charging port; wherein said base is provided with an electrical power cord extending from a side surface of said base; wherein said base is provided with a power converter located within said base; wherein said base is provided with a transformer located within said base; wherein said electrical power cord is in electrical connection with said transformer and said power converter; and, wherein a second set of electrical leads in electrical connection with said charging port are placed into electrical connection with said power converter and said transformer and extend to an outer surface of said charging port.

3. The telemetric device recited in claim 2, wherein said base further comprises a MODEM in electrical connection with said second set of electrical leads to modulate and demodulate wireless signals and communicate commands to said central processor.

4. The telemetric device recited in claim 1, further comprising an interface: wherein said interface is provided with a plurality of depression plates; wherein each of said depression plate is placed into electro-mechanical connection with a pressure sensor; wherein each of said pressure sensor is placed into electrical communication with a switching assembly; wherein said switching assembly is placed into electrical communication with said central processor; and, wherein said interface enables manual input-signals to be sent to said central processor.

* * * * *